United States Patent
Takatani et al.

(10) Patent No.: US 8,870,738 B2
(45) Date of Patent: Oct. 28, 2014

(54) CARDIAC FUNCTION CHANGE EVALUATING DEVICE

(75) Inventors: Setsuo Takatani, Tokyo (JP);
Yoshimasa Yokoyama, Tokyo (JP);
Thomas Schmitz-Rode, Aachen (DE);
Ulrich Steinseifer, Hauset (BE)

(73) Assignee: Reinheart GmbH, Bad Oeynhausen (DE)

( * ) Notice: Subject to any disclaimer, the term of this patent is extended or adjusted under 35 U.S.C. 154(b) by 61 days.

(21) Appl. No.: 12/598,849

(22) PCT Filed: May 9, 2008

(86) PCT No.: PCT/JP2008/058610
§ 371 (c)(1),
(2), (4) Date: Dec. 29, 2009

(87) PCT Pub. No.: WO2008/140034
PCT Pub. Date: Nov. 20, 2008

(65) Prior Publication Data
US 2010/0160801 A1    Jun. 24, 2010

(30) Foreign Application Priority Data

May 10, 2007 (JP) ................................ 2007-125477

(51) Int. Cl.
| | | |
|---|---|---|
| *A61N 1/362* | (2006.01) | |
| *A61M 1/10* | (2006.01) | |
| *A61B 5/0215* | (2006.01) | |
| *A61M 1/12* | (2006.01) | |
| *A61B 5/029* | (2006.01) | |
| *A61B 5/00* | (2006.01) | |

(52) U.S. Cl.
CPC .......... *A61B 5/0215* (2013.01); *A61M 2230/04* (2013.01); *A61M 1/122* (2014.01); *A61B 5/029* (2013.01); *A61B 5/6846* (2013.01); *A61M 1/101* (2013.01)
USPC .................................. 600/16; 600/17; 623/3.1

(58) Field of Classification Search
CPC ................ A61B 5/0215; A61B 5/029; A61M 2001/122; A61M 1/101
USPC ......................................... 600/16, 17; 623/3.1
See application file for complete search history.

(56) References Cited

U.S. PATENT DOCUMENTS

| 5,965,089 A * | 10/1999 | Jarvik et al. ..................... 422/44 |
| 6,171,253 B1 | 1/2001 | Bullister et al. |
| 6,227,797 B1 | 5/2001 | Watterson et al. |

(Continued)

FOREIGN PATENT DOCUMENTS

JP        2005-80982 A     3/2005

*Primary Examiner* — Niketa Patel
*Assistant Examiner* — William Levicky
(74) *Attorney, Agent, or Firm* — Andrew Wilford

(57) ABSTRACT

A cardiac function variation evaluation apparatus includes: a continuous flow type auxiliary artificial heart 20 connected to a ventricle (10A); a pressure sensor 30 for detecting ventricle (10A) internal pressure; and means (a personal computer 40) for evaluating contractile variation of the ventricle, to which the auxiliary artificial heart 20 is connected, based on internal area APMp of a closed-loop of a relationship between the ventricle internal pressure detected by the pressure sensor 30 and a consumption power of the auxiliary artificial heart 20. Thus, the contractile variation of the ventricle, to which an auxiliary artificial heart is connected, can be continuously evaluated not by use of an ultrasonic echo apparatus or a conductance catheter but by use of a non-invasive method.

4 Claims, 4 Drawing Sheets

(56) References Cited

U.S. PATENT DOCUMENTS

| | | |
|---|---|---|
| 6,264,601 B1 * | 7/2001 | Jassawalla et al. ............ 600/16 |
| 6,511,413 B2 * | 1/2003 | Landesberg .................... 600/17 |
| 6,572,530 B1 * | 6/2003 | Araki et al. .................... 600/17 |
| 6,949,066 B2 * | 9/2005 | Bearnson et al. ............... 600/16 |
| 2003/0191357 A1 * | 10/2003 | Frazier ........................... 600/16 |
| 2008/0183287 A1 | 7/2008 | Ayre ............................... 623/28 |
| 2009/0118625 A1 | 5/2009 | Hoshi et al. .................... 600/481 |

* cited by examiner

Fig. 1 - Prior Art

CARDIAC FUNCTION CHANGE EVALUATING DEVICE

CROSS REFERENCE TO RELATED APPLICATIONS

This application is the US national phase of PCT application PCT/JP2008/058610, filed 9 May 2008, published 20 Nov. 2008 as WO2008/140034, and claiming the priority of Japanese patent application 2007-125477 itself filed 10 May 2007, whose entire disclosures are herewith incorporated by reference.

FIELD OF THE INVENTION

The present invention relates to a cardiac function variation evaluation apparatus, more particularly, it relates to a cardiac function variation evaluation apparatus capable of continuously evaluating contractile variation of a ventricle to which an auxiliary artificial heart is connected, not by use of an ultrasonic echo apparatus or a conductance catheter inserted into the ventricle through a peripheral blood vessel but by use of a less invasive method.

BACKGROUND OF THE INVENTION

The applicant has proposed a continuous-flow auxiliary artificial heart constituted by a centrifugal pump, the auxiliary artificial heart being disclosed in Japanese Published Unexamined Patent Application No. 2007-44302. In the case where such an auxiliary artificial heart is connected, a cardiac function of a person having the connected auxiliary artificial heart sometimes recovers, and cardiac function variation, more particularly, contractile variation of a left ventricle, sometimes need to be evaluated.

On the other hand, as one of the methods for evaluating the cardiac function variation, more particularly, the contractile variation of the left ventricle, there is a method for inserting a conductance catheter into the left ventricle, calculating an internal area of a closed-loop from a relationship between left ventricle internal pressure and left ventricle internal volume, the relationship being indicated in FIG. 1, and then evaluating the cardiac function variation, the method being disclosed in Japanese Published Unexamined Patent Application No. 2002-143109. The closed-loop area (stroke volume) in FIG. 1 corresponds to workload.

However, in the conventional method, it is necessary to use an expensive ultrasonic echo apparatus or to insert the conductance catheter into the left ventricle of the person having the connected auxiliary artificial heart. Therefore, the method is invasive, and not only imposes a burden on the person, but also has a possibility of causing infection or a thrombus in the case of long-time use.

OBJECT OF THE INVENTION

The present invention was made in order to solve the above conventional problem, and aims at continuously evaluating contractile variation of a ventricle, to which an auxiliary artificial heart is connected, not by use of an ultrasonic echo apparatus or a conductance catheter but by use of a noninvasive method.

SUMMARY OF THE INVENTION

According to experiments by the inventors, it is possible to prepare a graph showing a relationship between left ventricle internal pressure and a motor consumption power as indicated in FIG. 3 based on a consumption power wave obtained by multiplying a current wave of a motor of a continuous-flow left ventricle auxiliary artificial heart 20 shown in FIG. 2 and motor voltage; and the internal pressure of a left ventricle 10A, the internal pressure being detected by a pressure sensor 30 built in a blood removal tube 22, and possible to, as indicated in FIG. 4, obtain a sufficient correlation between a closed-loop internal area APMp of the above relationship and an external work EW for circulating blood through the whole body including the left ventricle 10A and the auxiliary artificial heart 20. The correlation indicates that, regardless of characteristics of a pump of the artificial heart, the contractile variation of the left ventricle, to which the auxiliary artificial heart is connected, can be evaluated based on the closed-loop internal area APMp.

The present invention was made based on such knowledge, and solves the above problem by providing a cardiac function evaluation apparatus including: a continuous-flow auxiliary artificial heart connected to a ventricle; a pressure sensor for detecting the ventricle internal pressure; and means for evaluating contractile variation of the ventricle, to which the auxiliary artificial heart is connected, based on a relationship between the ventricle internal pressure detected by the pressure sensor and a consumption power of the auxiliary artificial heart.

Here, the contractile variation of the ventricle, to which the auxiliary artificial heart is connected, can be evaluated based on a closed-loop internal area of the relationship between the ventricle internal pressure and the consumption power of the auxiliary artificial heart.

Additionally, the pressure sensor can be built in a blood removal cannula for connecting the ventricle and the auxiliary artificial heart.

Additionally, as the auxiliary artificial heart, a diagonal flow pump, a centrifugal pump or an axial flow pump is applicable.

According to the present invention, it is possible to evaluate the contractile variation of the ventricle, to which the auxiliary artificial heart is connected, not by use of an ultrasonic echo apparatus or a conductance catheter but by use of a noninvasive method.

SPECIFIC DESCRIPTION OF THE INVENTION

Hereinafter, an embodiment of the present invention will be described in detail with reference to the drawings.

Figure 1:
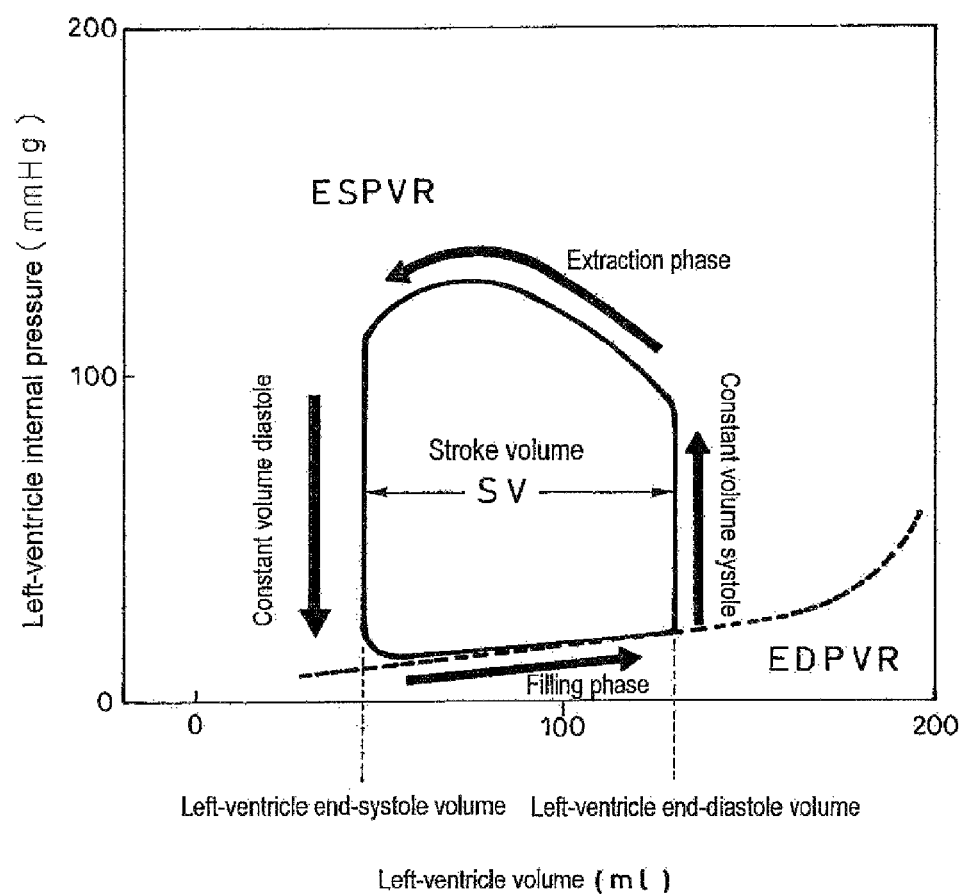
FIG. 1 is a graph showing one cycle using left ventricle internal pressure and a volume loop regarding the left ventricle according to the prior art.
Figure 2:
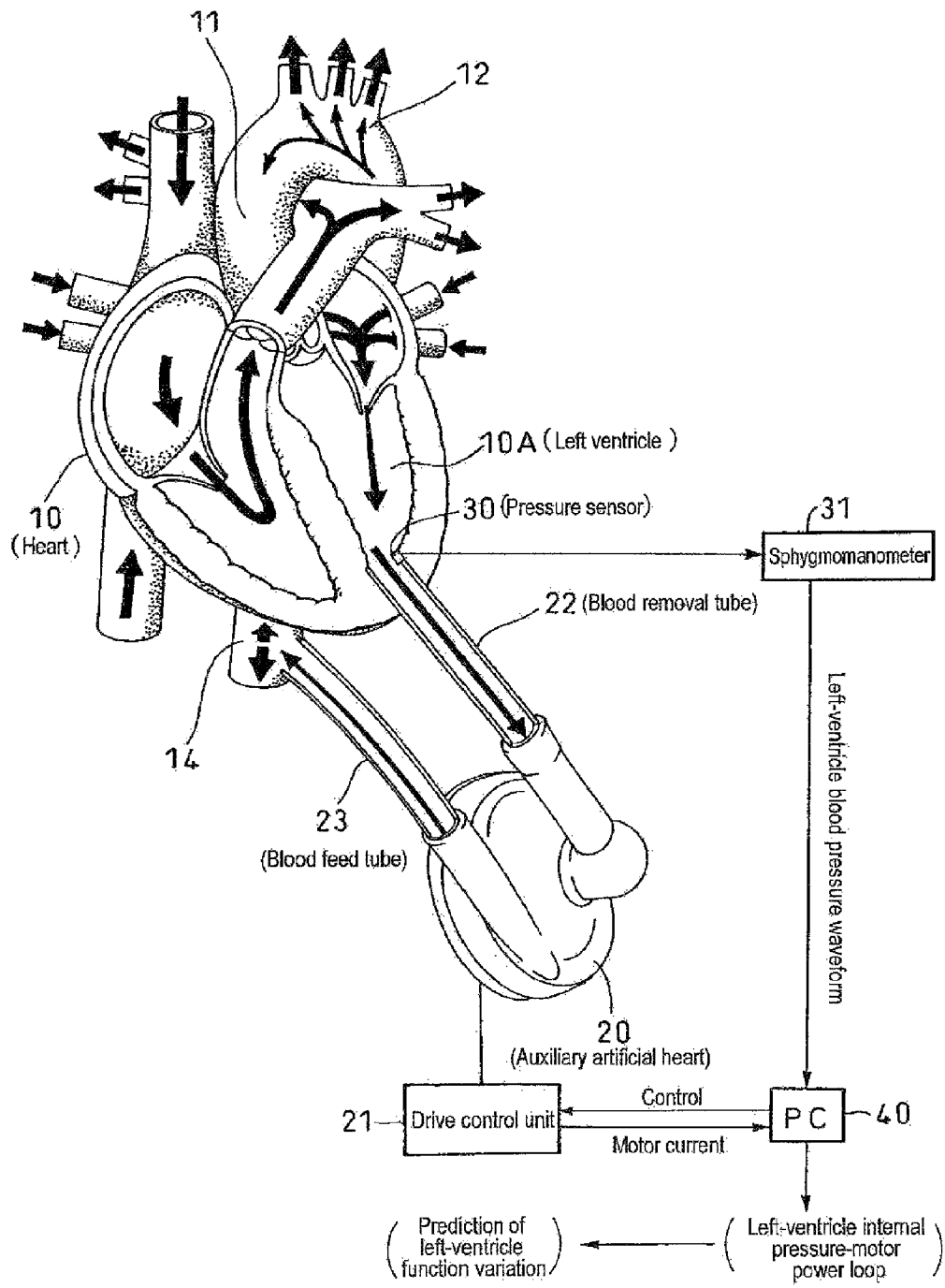
FIG. 2 is a view showing an embodiment of the present invention.

As shown in FIG. 2, a cardiac function variation evaluation apparatus of the embodiment includes: a continuous-flow auxiliary artificial heart 20 connected to a left ventricle 10A of a heart 10 and a drive controller 21 of the same; a pressure sensor 30 for detecting internal pressure of the left ventricle 10A and a sphygmomanometer 31; and a personal computer (PC) 40 for evaluating contractile variation of the left ventricle, to which the auxiliary artificial heart is connected, based on a closed-loop internal area APMp of a relationship between the left ventricle internal pressure detected by the pressure sensor 30 and a motor consumption power of the auxiliary artificial heart 20.

In FIG. 2, the reference symbol 11 denotes an ascending aorta, 12 denotes an aortic arch, 14 denotes a descending aorta, and 23 denotes a blood feed tube.

As the auxiliary artificial heart 20, a diagonal flow pump is usable, for example. Alternatively, a centrifugal pump or an axial flow pump, etc., may be used.

It is desirable that the pressure sensor 30 is provided on an wall at the top end of a blood removal cannula 22 for connecting the left ventricle 10A and the auxiliary artificial heart 20, the wall being in the vicinity of the ventricle.

Figure 3:
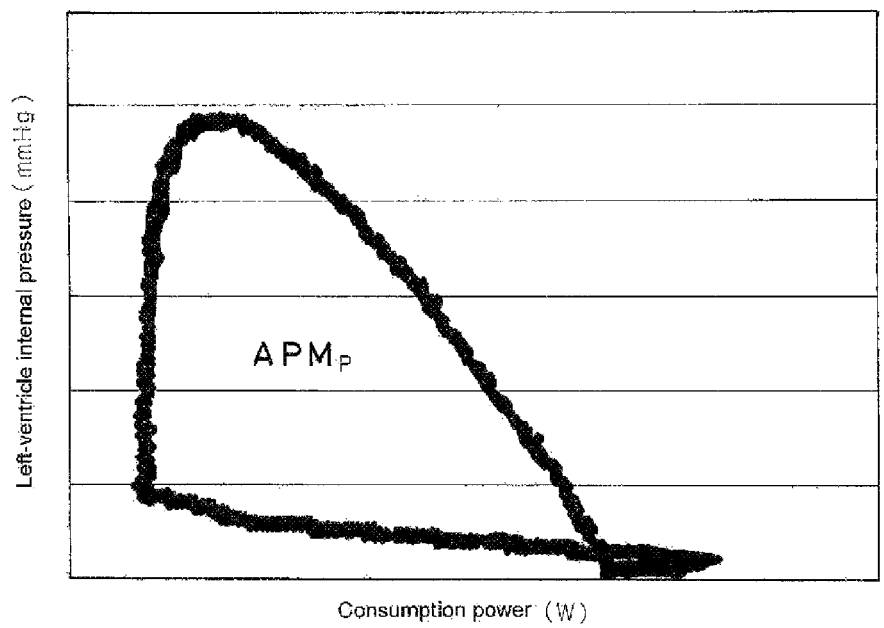
FIG. 3 is a graph showing a relationship between the left ventricle internal pressure and motor consumption power of an auxiliary artificial heart, the relationship explaining the principle of the present invention.

A graph showing the relationship illustrated in FIG. 3 between the left ventricle internal pressure and the motor consumption power is prepared based on the motor consumption power of the auxiliary artificial heart 20 and an output of the pressure sensor 30, which are calculated by using a simulated circulation circuit or a conventional conductance catheter and the like in an animal experiment. Then, a relationship between the calculated closed-loop internal area APMp and a loop internal area of the left ventricle pressure and volume which is calculated by using a conventional conductance catheter and the like, is obtained in advance, and a relational expression as indicated in FIG. 4 is prepared.

Figure 4:
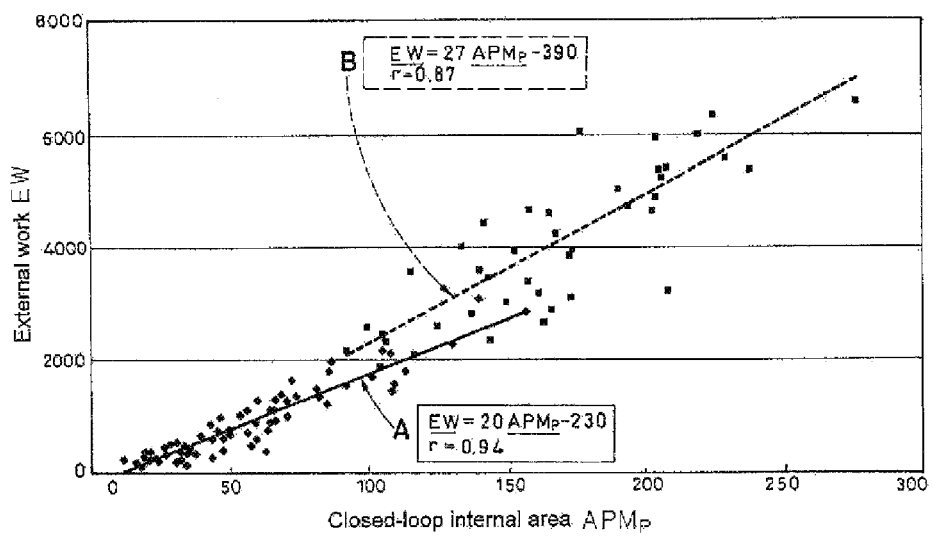
FIG. 4 similarly is a graph showing an example of a relationship between a closed-loop internal area APMp calculated based on the motor consumption power and an external work calculated based on the left ventricle internal pressure and the volume loop.

As shown in FIG. 2, in a full bypass state in which the heart is weak and a valve is not opened, a high correlation (correlation coefficient: r=0.94) as indicated by a solid line A in FIG. 4, is obtained in which an external work EW is small relative to the closed-loop internal area APMp.

$$\text{Solid line } A: EW = 20 \, APMp - 230 \quad (1)$$

Figure 5:
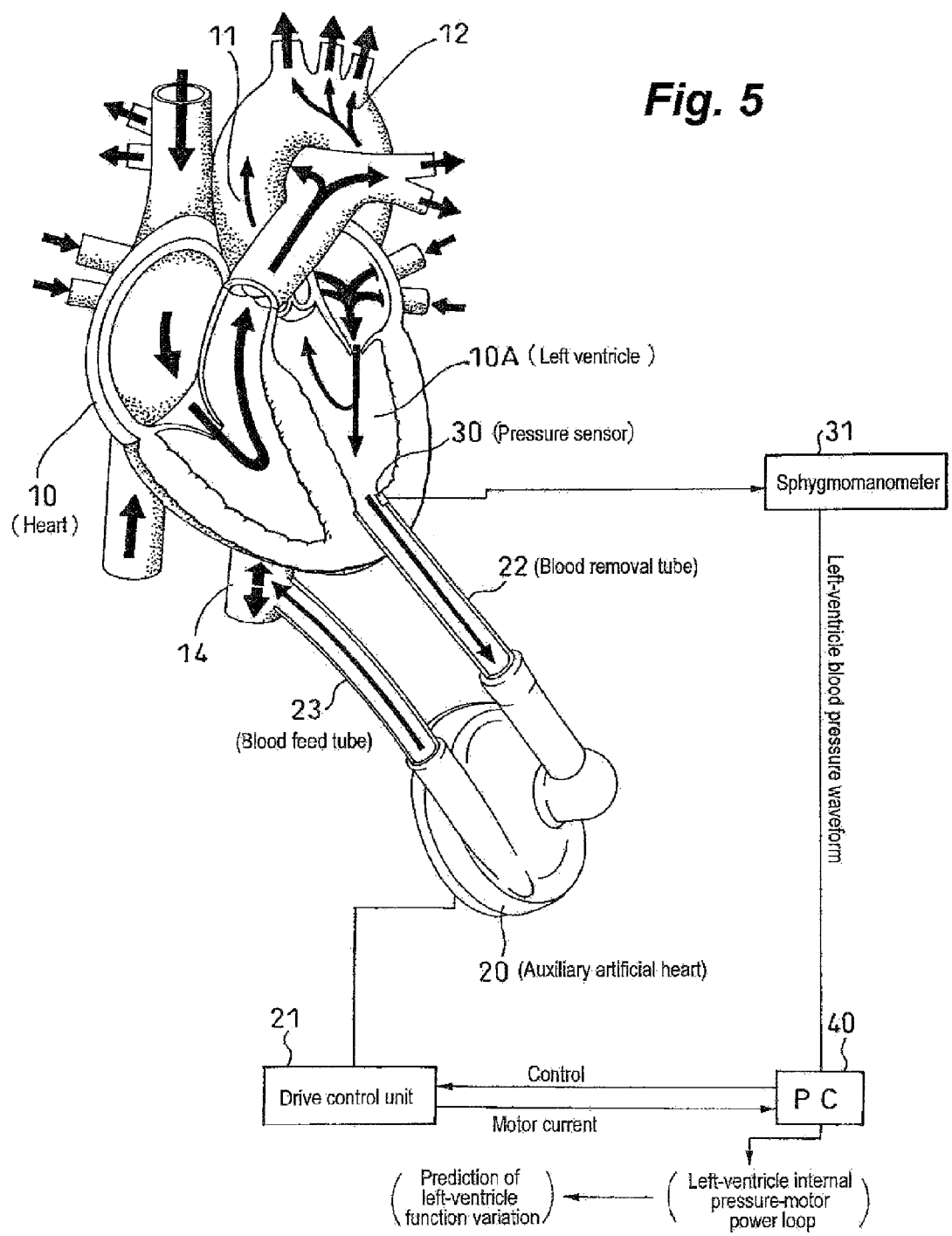
FIG. 5 is a view showing a partial bypass state of the embodiment.

On the other hand, in the case of a partial bypass state where the heart recovers and an aorta valve is opened as shown in FIG. 5, the external work EW becomes relatively high and the correlation becomes slightly worse (correlation coefficient: r=0.87) as indicated by a broken line B in FIG. 4.

$$\text{Broken line } B: EW = 27 \, APMp - 390 \quad (2)$$

Accordingly, if variation of the closed-loop internal area APMp is continuously monitored, it suggests that the contractile variation of the left ventricle can be presumed.

Moreover, although the diagonal flow pump is employed as the auxiliary artificial heart in the embodiment, the present invention is not limited to it. The present invention is also applicable to the centrifugal pump, or the axial pump.

INDUSTRIAL APPLICABILITY

The present invention is usable for the case of continuously evaluating contractile variation of a ventricle, to which an auxiliary artificial heart is connected, not by use of an ultrasonic echo apparatus or a conductance catheter to be inserted into the ventricle through a peripheral blood vessel but by use of a noninvasive method.

The invention claimed is:

1. A cardiac function variation evaluation apparatus comprising:
   a power-consuming continuous-flow auxiliary artificial heart of the bypass type connectable to a left ventricle;
   a pressure sensor also connectable to the left ventricle for detecting ventricle internal pressure;
   means for detecting power consumption of the auxiliary heart by multiplying a current wave of the motor and voltage of the motor; and
   means for calculating the contractile variation of the left ventricle to which the auxiliary artificial heart is connectable by
      continuously monitoring the variation of the closed loop internal area of a relationship between the ventricle internal pressure detected by the pressure sensor and the detected power consumption of the auxiliary artificial heart, and
      basing the calculation also on a correlation between the internal area of a closed loop of the relationship and an external work capable of circulating blood through a whole body including the left ventricle and the auxiliary artificial heart, the correlation being high in a full bypass state in which the heart is weak and the aortic valve is not open and being worse in a partial bypass state in which the heart recovers and an aortic valve is open.

2. The cardiac function variation evaluation apparatus according to claim 1 wherein the contractile variation of the ventricle, to which the auxiliary artificial heart is connected, is evaluated based on an internal area of a closed-loop of the relationship between the ventricle internal pressure and the consumption power of the auxiliary artificial heart.

3. The cardiac function variation evaluation apparatus according to claim 1 wherein the artificial heart includes a blood-removal cannula and a pressure sensor built into the blood-removal cannula via which the auxiliary artificial heart is connectable to the ventricle.

4. The cardiac function variation evaluation apparatus according to claim 1 wherein the auxiliary artificial heart is a diagonal flow pump, a centrifugal pump or an axial flow pump.

* * * * *